(12) United States Patent
Tajima et al.

(10) Patent No.: US 6,787,364 B2
(45) Date of Patent: Sep. 7, 2004

(54) SAMPLE CHIP ANALYZING DEVICE AND METHOD FOR ANALYZING THE SAME

(75) Inventors: Haruo Tajima, Nagoya (JP); Hidekatsu Yoneda, Nagoya (JP)

(73) Assignee: Nippon Laser & Electronics Lab., Nagoya (JP)

( * ) Notice: Subject to any disclaimer, the term of this patent is extended or adjusted under 35 U.S.C. 154(b) by 293 days.

(21) Appl. No.: 09/847,548

(22) Filed: May 2, 2001

(65) Prior Publication Data

US 2002/0003623 A1 Jan. 10, 2002

(30) Foreign Application Priority Data

Jul. 6, 2000 (JP) ........................................ 2000-205265

(51) Int. Cl.[7] .............................................. G01N 31/00
(52) U.S. Cl. ..................... 436/86; 436/172; 422/68.1; 422/82.05; 422/82.08; 422/82.11
(58) Field of Search ............................. 422/68.1, 82.05, 422/82.08, 82.11; 436/86, 172

(56) References Cited

U.S. PATENT DOCUMENTS 5,633,724 A * 5/1997 King et al. ................. 356/445

FOREIGN PATENT DOCUMENTS

JP          10-221339          8/1998

* cited by examiner

Primary Examiner—Jill Warden
Assistant Examiner—Sam P. Siefke
(74) Attorney, Agent, or Firm—Frishauf, Holtz, Goodman & Chick, P.C.

(57) ABSTRACT

A sample chip analyzing device includes a waveguide plate which entirely reflects and guides incident light and has a number of sampling probes that are connectable to a sample to be analyzed, a light source which irradiates fluorescent pumping light onto an end face of an end portion of the waveguide plate that is inserted into a light-shielding box, and a pickup member which picks up an image of substantially an entire surface of the waveguide plate. The sample to be analyzed is labeled with fluorescent substances that are fluorescence-pumped by an evanescent wave which occurs when the fluorescent pumping light enters into an interior of the waveguide to be entirely reflected and guided, and the sample is analyzed by detecting respective ones of the sampling probes that are coupled to the fluorescence-pumped flourescent substances of the labeled sample, based on data outputted by the pickup member.

3 Claims, 4 Drawing Sheets

SAMPLE CHIP ANALYZING DEVICE AND METHOD FOR ANALYZING THE SAME

DETAILED DESCRIPTION OF THE INVENTION

1. Field of the Invention

The present invention relates to a sample chip analyzing device and a method for analyzing the sample chip that analyzes gene generating modes of cells and biological tissues and analyzes antigen and antibody reactions.

2. Themes to be Solved by the Invention

In the abovementioned use, a sample chip has been used, in which various types of sample probes such as polynucleotide and protein peptide probes like a DNA probe, an RNA probe, etc., are dot-arrayed and fixed on a glass sheet slide at high density (several tens through seven ten thousands pieces per square centimeter).

For example, in the work of analyzing gene generating modes, a test sample to be analyzed, which is extracted from cells and biological tissues, adjusted, and marked with a fluorescent substance, is adhered to respective sampling probes on a sample chip. Where the sampling probe and the test sample to be analyzed are complementary to each other, they are coupled to each other. To the contrary, where they are not complementary to each other, they are not coupled.

After the sample to be analyzed, which has not been coupled to the sampling probe, is washed off by a buffer solution, the surface of the sample chip is optically scanned, and fluorescence from the marked fluorescent substances is detected to specify the sample to be analyzed, by the sampling probe to which the sample to be analyzed is coupled.

When optically scanning the sample chip, light of an appointed beam diameter is irradiated thereto from a light source, and at the same time an objective lens, which receives light from a sample chip, and the sample chip are caused to move relative to each other in order to scan the entirety thereof, whereby the marked fluorescent substances of the hybridized sample to be analyzed are pumped.

In the abovementioned method, since reflected pumping light of the fluorescent substance is received together with the fluorescence from the fluorescent substance, it is necessary to provide an optical filter to distinguish the fluorescence from the pumping light. However, since the reflected pumping light is remarkably intense in comparison with the fluorescence, the fluorescence detection is likely to be influenced by the pumping light, wherein the fluorescence detection accuracy was not satisfactory.

Although it is necessary to widen the light receptive area by increasing the diameter of the objective lens to efficiently receive the fluorescence pumped or excited by the fluorescent substance, a light irradiating apparatus became large in size.

Further, in order to raise the detection accuracy of fluorescence by suppressing disturbance light (noise), it is necessary to approach the objective lens to the sample chip. But, there is a limitation in the approaching distance due to the physical properties of the objective lens, wherein the fluorescence could not be detected at high accuracy.

The present invention was developed to solve the abovementioned problems and shortcomings in the prior art. It is therefore an object of the invention to provide a sample chip analyzing device and a method for analyzing the sample chip, which are capable of detecting, at high accuracy, fluorescence from marked fluorescent substances of a sample to be analyzed, which have been coupled to a sampling probe, without being influenced by pumping light of the fluorescent substance and disturbance light (noise), and efficiently analyzing the sample to be analyzed.

In addition, it is another object of the invention to provide a sample chip analyzing device and a method for analyzing the sample chip, which are capable of detecting fluorescence of different wavelengths at one time and efficiently analyzing the sample to be analyzed.

EMBODIMENTS OF THE INVENTION

Hereinafter, a description is given of embodiments of the invention with reference to the accompanying drawings.

Figure 1:
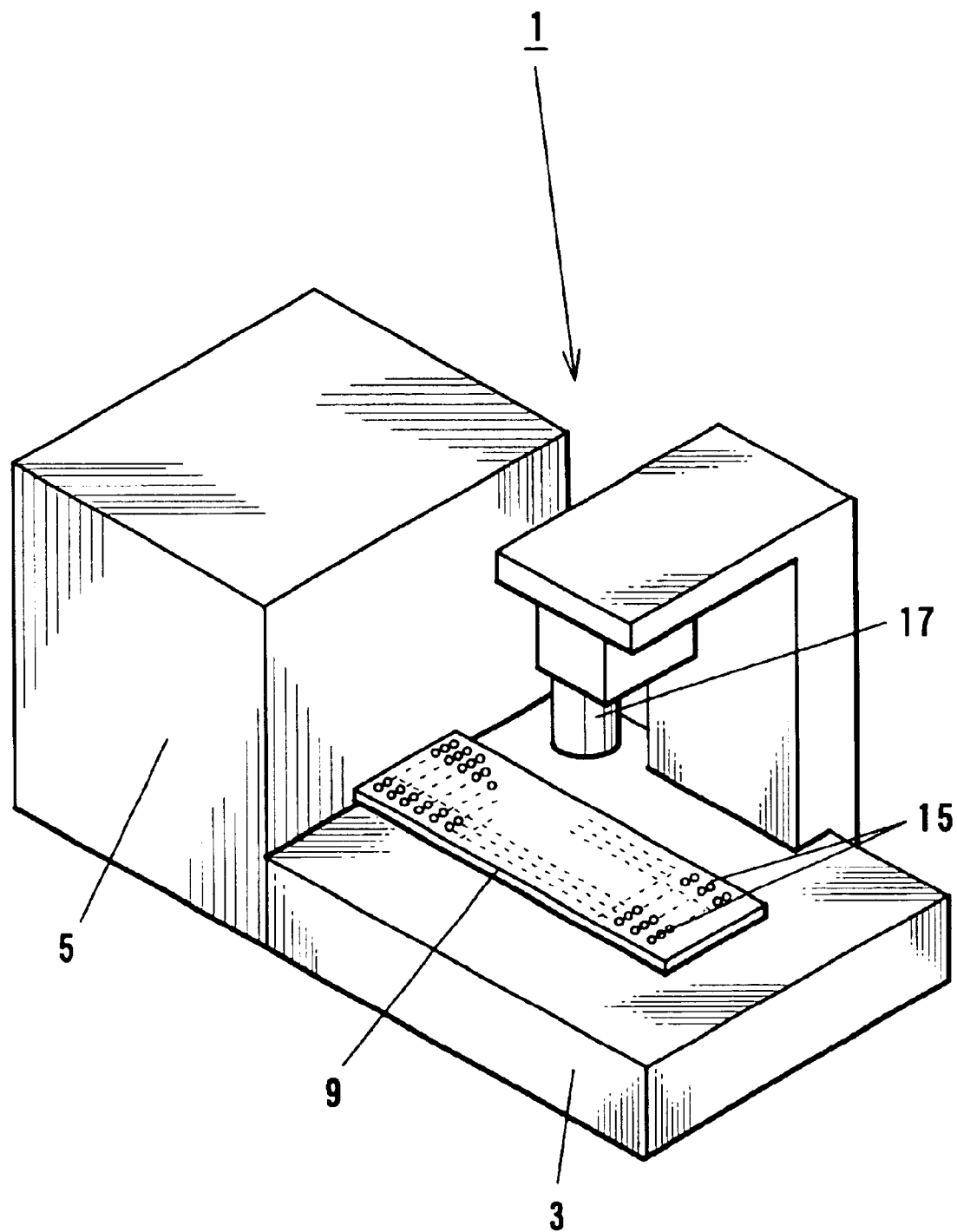
FIG. 1 is a perspective view showing the entire sample chip analyzing device.
Figure 2:
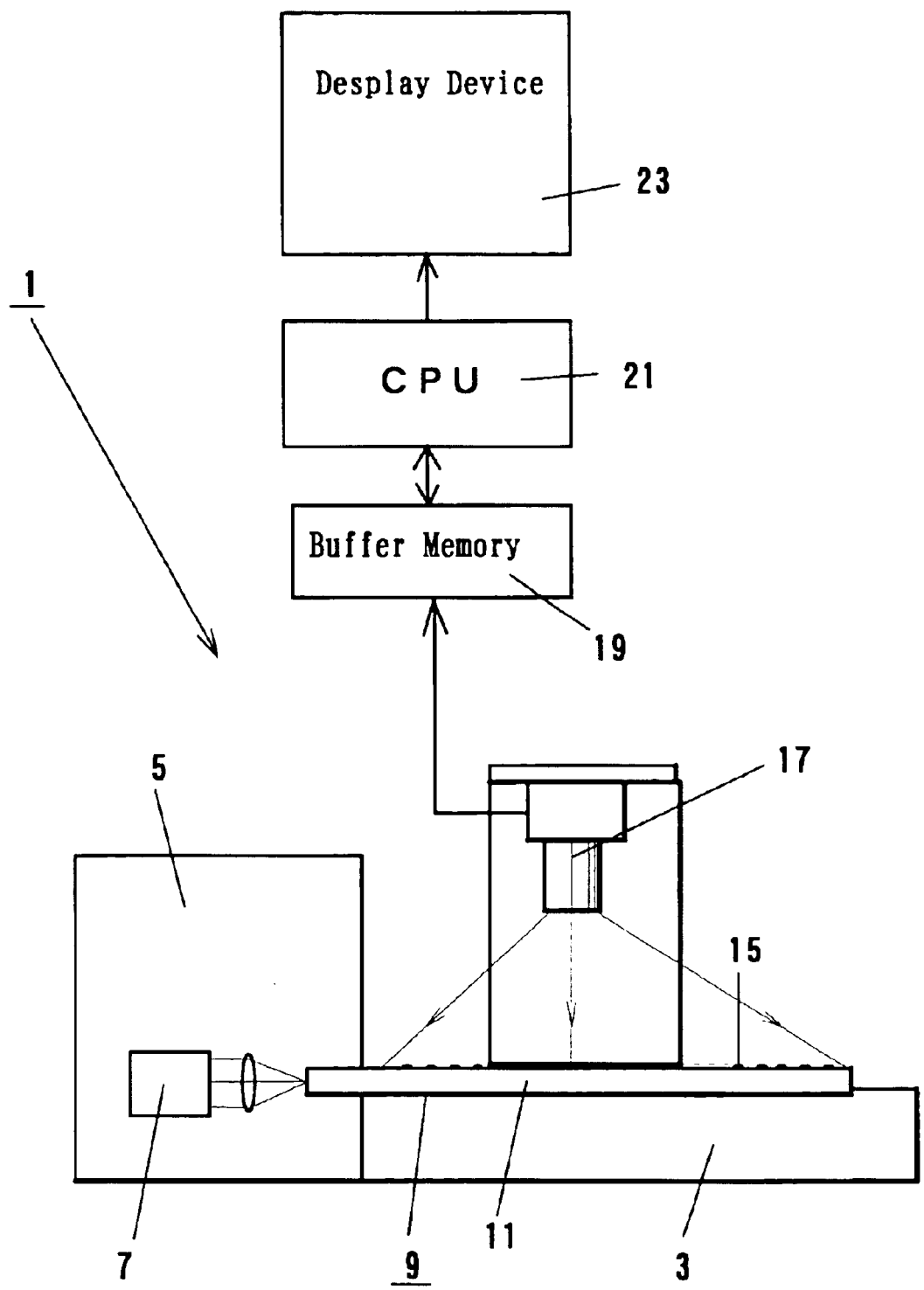
FIG. 2 is a view showing the principle of the analyzing device.
Figure 3:
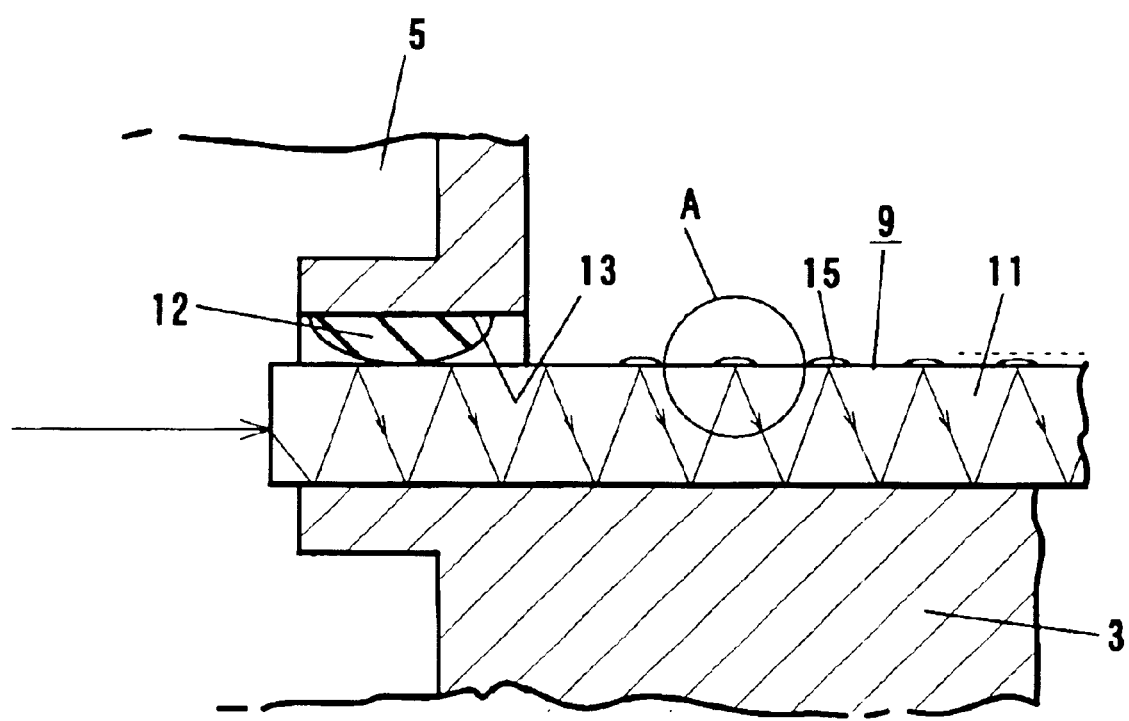
FIG. 3 is a view describing a waveguide of light on a glass sheet slide.

In FIG. 1 and FIG. 3, a light shielding box 5 is installed at the side of a table 3 of a sample chip analyzing device 1. A light source 7 is internally incorporated in the light shielding box 5. Also, an opening into which a waveguide plate 11 of a sample chip 9 described later is inserted in a close-adhered state is formed at the light shielding box 5, and the end portion of the waveguide plate 11 placed on a table 3 is inserted into the opening 13.

In the drawings, 12 denotes a packing adhered to the inner-circumferential surface of the opening 13, which prevents light from the light source 7 described later from leaking outside of the waveguide 11.

The light source 7 is determined by a wavelength that pumps a fluorescent substance marked on a sample to be analyzed, which is described later. For example, in the case where the marked fluorescent substance for the sample to be analyzed is single, the light source 7 may be a laser irradiating device that outputs light of a specified wavelength by which the corresponding fluorescent substance is pumped or in the case where a plurality of marked fluorescent substances are used, any one that outputs white light of respective pumping wavelengths may be acceptable.

The sample chip 9 set on the table 3 is such that a number of sampling probes 15 such as polynucleotide probes like DNA probes and RNA probes and protein peptide probes are fixed, at the waveguide plate 11 in which glass sheet slides or thin glass plates having an optical waveguide property, like dots at high density (several thousands to several ten thousands per square centimeter).

A pickup device 17 that photographs the surface of the sample chip 9 is arranged above the sample chip 9 set on the table 3. As the corresponding pickup device 17, for example, a CCD camera is suitable, which can photograph the entire sample chip 9 as one frame or photograph the sample chip section by section with a plurality of frames.

Further, RGB filters is incorporated in the pickup device 17, and the corresponding RGB filters decomposes the pickup data color by color, and the color pickup data are stored in a buffer memory 19. And the central processing unit (CPU) 21 outputs the pickup data of the respective colors, which are stored in the buffer memory 19, and displays the entire image of the sample chip 9.

Next, a description is given of the method for analyzing a sample to be analyzed, by the abovementioned sample chip analyzing device.

Figure 4:
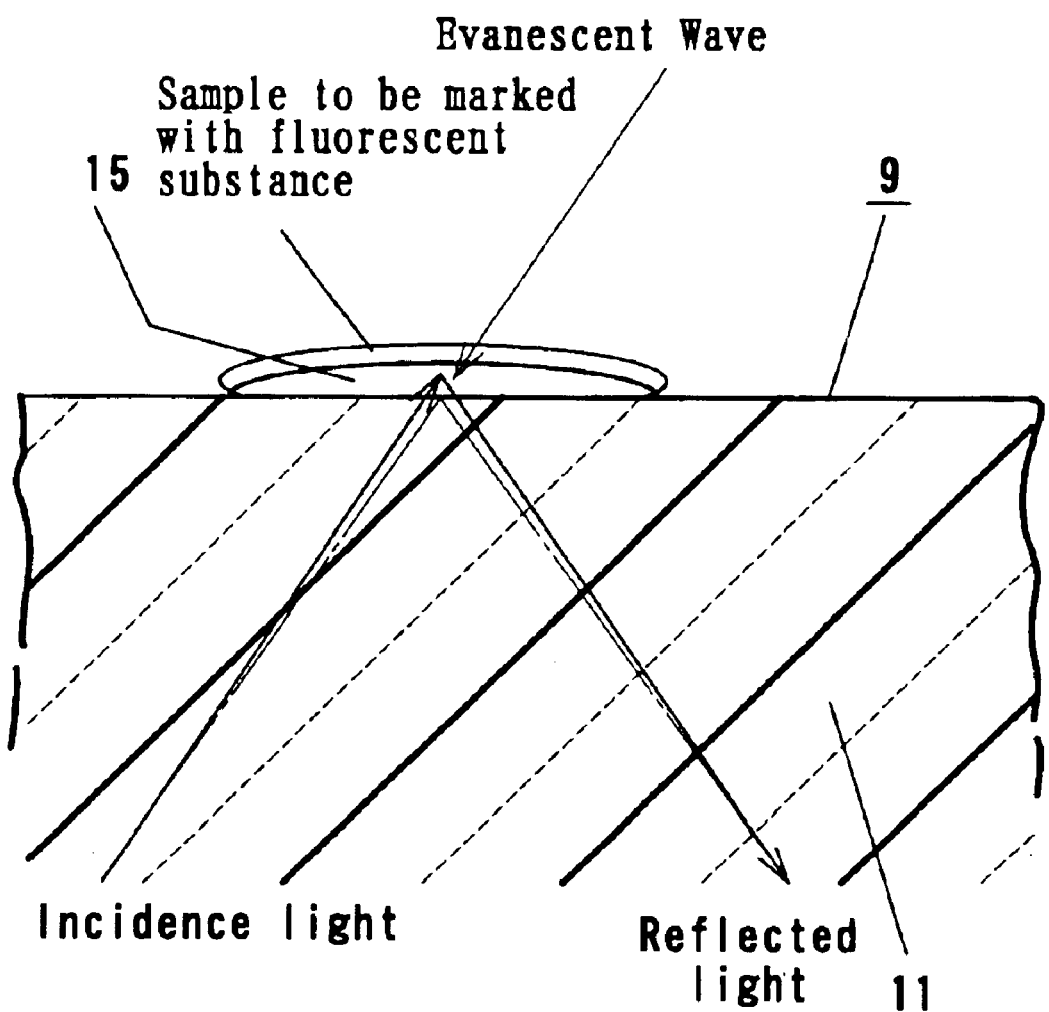
FIG. 4 is an enlarged view of part "A" in FIG. 3.

The following description is based on a DNA analysis example. In FIG. 3 and FIG. 4, in order to hybridize a sample to be analyzed, on which a fluorescent substance is marked, with respect to the sampling probe 15 arrayed and fixed on the sample chip 9, a buffer solution containing a sample to be analyzed, which is extracted from cells and biological tissues, adjusted, and marked with a fluorescent substance, is adhered to the surface of sample chip 9, and is left in an appointed period of time as it is. At that time, where the sample to be analyzed and sampling probes 15 are complementary to each other, they are hybridized to become a two-chain structure. To the contrary, where they are not complementary to each other, they are not coupled to each other.

After the abovementioned appointed period of time elapses, the upper surface of the sample chip 9 is washed off by pure water or a buffer solution to remove the sampling probes 15 and non-coupled samples to be analyzed.

Next, after the sample chip 9 is set so that the end part thereof is inserted into the opening 13, light from the light source 7 is made incident from the end plane of the waveguide plate 11 into the interior thereof, whereby the light incident into the waveguide plate 11 is entirely reflected when the incident angle thereof exceeds the incident critical angle, and the light is guided to the other end part side of the sample chip.

At this time, an evanescent wave is generated on the surface and rear planes of the sample chip 9 by light that is entirely reflected in the interior of the waveguide plate 11, and a part thereof leaks out of the surface of the sample chip 9, wherein the electric field pumps the marked fluorescent substances of the sample to be analyzed, which is hybridized to the sampling probes 15 by the electric field, and the fluorescent substance fluoresces.

At this time, if the marked fluorescent substances of the sample to be analyzed, which is hybridized to respective sampling probes 15 of the sample chip 9, differ from each other, white light that is mixed by RGB may be used as the light source 7, and the respective fluorescent substances are caused to fluoresce by the respective colors. In this case, since the pumping energy of the respective fluorescent substances is low, it is necessary to increase the output of the light source.

Using the pickup device 17, an operator picks up an image of the surface of the sample chip in which the marked fluorescent substances fluoresce, and displays it on a display device 23, wherein the fluoresced sampling probes are discriminated, the samples to be analyzed, which are hybridized to the sampling probes are specified and analyzed.

Since, in the abovementioned embodiment, the marked fluorescent substances of a sample to be analyzed, which are hybridized to the sampling probes 15 by an evanescent wave occurring when light advances in the interior of the waveguide plate 11 while being entirely reflected, are caused to fluoresce, there is no case where the reflected pumping light is received together with the fluorescence, in comparison with a prior art method in which light (pumping light) is irradiated from the outside to respective sampling probes and fluorescence from the fluorescent substances is received. Therefore, it is possible to shield influences of the pumping light and efficiently detect only the fluorescence, wherein it becomes possible to improve the analysis accuracy.

Also, in order to specify the samples to be analyzed, by discriminating the fluorescing sampling probes 15 from the pickup data on the surface of the sample chip 9, the time required for analysis can be remarkably shortened in comparison with the prior art method in which scanning is carried out by light.

What is claimed is:

1. A sample chip analyzing device comprising:

a waveguide plate which entirely reflects and wave-guides incident light, and which includes a surface on which a number of sampling probes are fixed, the sampling probes being coupled to samples to be analyzed that are labeled with a fluorescent substance;

a light source, provided in a light-shielding box having an opening into which an end portion of the waveguide plate is inserted in a light-shielded state, for introducing fluorescent excitation light into the waveguide plate through the end portion of the waveguide plate inserted into the light-shielding box; and a pickup member for picking up an image of substantially an entire surface of the waveguide plate, and outputting picked-up data of fluorescence;

wherein the fluorescent substance labeled on the samples coupled to the probes is excited by an evanescent wave generated when the waveguide plate wave-guides the fluorescent excitation light from the light source into an interior of the waveguide plate, and entirely reflects the fluorescent excitation light; and wherein the samples are analyzed by detecting respective ones of the sampling probes that are coupled to the labeled samples, based on the picked-up data of fluorescence outputted by the pickup member.

2. The sample chip analyzing device according to claim 1, wherein the waveguide plate comprises a glass substrate.

3. The sample chip analyzing device according to claim 1, wherein the waveguide plate comprises a pair of spaced apart insulation reflection plates arranged opposite to each other.

* * * * *